United States Patent [19]

Krahler

[11] Patent Number: 4,489,006

[45] Date of Patent: Dec. 18, 1984

[54] IODOPENTAHYDROPERFLUOROALKYL BORATES

[75] Inventor: Stanley E. Krahler, Wilmington, Del.

[73] Assignee: E. I. Du Pont de Nemours and Company, Wilmington, Del.

[21] Appl. No.: 599,212

[22] Filed: Apr. 12, 1984

Related U.S. Application Data

[63] Continuation of Ser. No. 470,174, Feb. 28, 1983, abandoned.

[51] Int. Cl.$^3$ .................................................. C07F 5/02
[52] U.S. Cl. .................................... 260/462 R; 568/842
[58] Field of Search .................................... 260/462 R

[56] References Cited

U.S. PATENT DOCUMENTS

| | | | |
|---|---|---|---|
| 2,523,433 | 9/1950 | Irany | 260/462 R |
| 2,568,859 | 9/1951 | Ladd et al. | 260/462 R X |
| 2,951,871 | 9/1960 | Schroeder | 260/462 R |
| 3,020,307 | 2/1962 | Luvisi | 260/462 R |
| 3,020,309 | 2/1962 | Luvisi | 260/462 R |
| 3,299,173 | 1/1967 | Roselli | 260/462 R X |
| 4,283,533 | 8/1981 | Richter | . |
| 4,388,212 | 6/1983 | Richter | . |

*Primary Examiner*—Helen M. S. Sneed

[57] ABSTRACT

2-Iodo-1,1,2,3,3-pentahydroperfluoroalkyl borates, their preparation from perfluoroalkyl iodides and triallyl borate in the presence of a free radical initiator, and preparation of perfluoroalkylpropylene iodohydrins by hydrolysis of the borates.

19 Claims, No Drawings

IODOPENTAHYDROPERFLUOROALKYL BORATES

CROSS REFERENCE TO RELATED APPLICATIONS

This application is a continuation of application Ser. No. 470,174 filed Feb. 28, 1983, now abandoned.

BACKGROUND OF THE INVENTION

1. Field of the Invention

This invention relates to 2-iodo-1,1,2,3,3-pentahydroperfluoroalkyl borates and their preparation from perfluoroalkyl iodides and triallyl borate in the presence of a free radical initiator. It relates also to the process of preparing perfluoroalkylpropylene iodohydrins by hydrolysis of the borates of this invention.

2. Description of the Prior Art

Japanese Pat. No. 79011284 to Daikin Kogyo discloses the $\alpha,\alpha'$-azobisisobutyronitrile (AIBN) initiated addition of perfluoroalkyl iodides to allyl alcohol, at a molar ratio of $R_fI$ to allyl alcohol of 0.5:1.0 and a molar ratio of AIBN to $R_fI$ of 0.10.

N. O. Brace reported in J. Organic Chemistry 27, 3033 (1962) the addition of 1-iodoperfluoropropane to allyl acetate, initiated by 0.02 mole AIBN per mole of $C_3F_7I$.

This invention provides several advantages over the prior art. Higher conversions are obtained in less reaction time with the process of this invention. Lower levels of the free radical initiators are used in this invention, thus minimizing by-product formation. Because of similarities in boiling points, unreacted iodide is difficult to separate from the borate or iodohydrin products. The borates of this invention and the iodohydrins prepared from them are of high purity, as there is little unreacted material.

DETAILED DESCRIPTION OF THE INVENTION

According to one aspect of this invention, at least one perfluoroalkyl iodide is reacted with triallyl borate in the presence of a free radical initiator to yield a mixture of products in which some or all of the allyl radicals are converted to 2-iodo-1,1,2,3,3-pentahydroperfluoroalkyl groups:

$R_fI + (CH_2=CHCH_2O)_3B \longrightarrow$

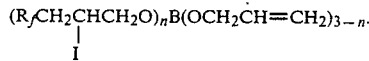

The borates of this invention can be converted by aqueous hydrolysis to boric acid and iodohydrins having the formula:

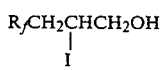

wherein $R_f$ is $C_4$–$C_{20}$ perfluoroalkyl and n is an average number between 1.5 and 3.

The iodohydrins can be used to prepare fluorosurfactants, such as those described by Katsushima et al. in U.S. Pat. No. 4,165,338; by Richter, in U.S. Pat. No. 4,283,533, or by Krahler et al. in a U.S. application Ser. No. 454,589, filed Dec. 30, 1982.

This invention contemplates single borate compounds having the foregoing formula as well as mixtures thereof. Usually, the latter are prepared and used because the starting material which provides the perfluoroalkyl portion of the molecule is most commonly available commercially as a mixture. The usual commercial mixture will contain small amounts (less than 5% by weight) on both ends of the foregoing carbon chain length range, with 80 to 90% of the chains containing 6 to 12 carbons, preferably 6 to 10 carbons, with an average of the chain lengths in the mixture being between 6 and 8 carbons.

The reaction between $R_fI$, or mixtures thereof, and triallyl borate can be run at almost any mol ratio. Generally, it is run at an $R_fI:B(OCH_2CH=CH_2)_3$ mol ratio between about 1.5:1 and 3:1. Below 1.5:1, too much allyl alcohol needs to be recovered and purified. At 3:1, conversion is satisfactory with $C_6F_{13}I$ and $C_8F_{17}I$; the higher homologs of $R_fI$ convert slightly more slowly. There is evidence that steric packing makes the synthesis of $(R_fCH_2CHICH_2O)_3B$ more difficult when $C_{10}F_{21}I$ and higher homologs are present. Therefore, a mole ratio between about 1.7 and 2.5 is more practical, with one between about 1.7:1 and 2:1 being preferred.

The $R_fI/B(OCH_2CH=CH_2)_3$ reaction can be run neat or in the presence of a solvent, preferably neat. For example, one may use an aromatic hydrocarbon such as benzene or toluene; a perhaloalkane or perhaloalkylene, such as 1,1,2-trichloro-1,2,2-trifluoroethane or perchloroethylene; or an aprotic polar solvent, such as methyl ethyl ketone.

The only real constraint on the temperature at which the reaction is run is the half-life of the free radical initiator. The free radical initiator which is usually used is an azo compound, but peroxy compounds may be used, e.g. $\alpha,\alpha'$-azobis-(isobutyronitrile); 2,2'-azobis-(2,4-dimethylvaleronitrile); 2-t-butylazo-2-cyanopropane; t-butylperoxypivalate. Generally temperatures in the range between about 50° and 140° can be used; a range of about 60° to 85° is more usual, with the preferred range being between about 65° and 75°. The reaction is advantageously carried out at atmospheric pressure; however, elevated pressures may be used.

The reaction of triallyl borate with $R_fI$ may produce a mild exotherm which can be controlled using conventional cooling techniques and equipment. For example, reflux with appropriate condensing equipment can be used when the reaction is carried out in a solvent. When run neat the reactor can itself be cooled if necessary. The exotherm, if any, is such that the starting materials can be simply mixed with one another without resorting to dropwise addition.

When run neat, the borate product of this invention is recovered as a melt and then allowed to solidify. When run in a solvent, the borate product on cooling will be only partially soluble in the solvent. It is usually sufficient to recover it without further purification; i.e. partially in solution and partially as a precipitate.

The hydrolytic instability of boric acid esters is well known. The borates of this invention being no different in this than known borates, a means of hydrolyzing the borates of this invention is readily provided. One can drown the borate product in water by adding it to water or adding water to it. Drowning of the borate product is carried out at a temperature above the freezing point of the borate to give a water-insoluble iodohydrin and water-soluble by-product boric acid. A small amount of sodium chloride can be used to facilitate clean separation of the phases.

The following examples are given by way of illustration not limitation. Unless specified otherwise, all parts and percentages are by weight and temperatures are in degrees centigrade. The preparation of triallyl borate made for Example 1 is typical of preparations made for Examples 2–5 and 7.

EXAMPLE 1

Preparation of Triallyl Borate

A mixture of 61.8 g. (1.0 mole) of boric acid, 232 g. (4.0 moles) of allyl alcohol and 121 g. of toluene was refluxed at a pot temperature of 91°–127° and atmospheric pressure, using a 1"×14" column packed with 6 mm. glass beads to effect separation, and a Dean-Stark separator to remove the by-product water from the solvent. Reflux was continued until no more water was collected in the Dean-Stark separator (~24 hrs). Additional allyl alcohol (58 g.; 1.0 mole) was added and the mixture was refluxed for 5 hrs.; no additional water evolved. The product mixture was topped to a pot temperature of 127° to remove toluene and excess alcohol. The residue was distilled in vacuo through a 5-plate Oldershaw column to yield 151 g. (83% of theory) of a colorless liquid product distilling at 72°–73° and 7.4–8.8 mm absolute mercury pressure.

Adduct Formation

A mixture of perfluorohexyl iodide (99.8 pure by gas chromatographic assay) (200 g.; 0.448 mole) and triallyl borate (6 g.; 0.033 mole) was heated to 63° under agitation in a pre-dried 250-ml. reaction flask, back diffusion of moisture being prevented by oversurface nitrogen sweep. Azobisisobutyronitrile (AIBN) (0.4 g.; 0.0024 mole) was added. No exotherm was observed on mixing or on heating to 72±2° over 0.75 hr. Dropwise addition of triallyl borate (21.2 g.; 0.116 mole) (final mol ratio of $R_fI$ to triallyl borate of 3.0:1.0) required approximately 0.5 hr. Upon completion of the addition, the charge was heated under agitation to 75°; a modest exotherm was observed, the charge temperature rising to 77°. The temperature was adjusted to 75±1° and held in that range for 1.5 hrs. AIBN (0.4 g.; 0.0024 mole) was added and the charge was agitated at 75±1° for 17.5 hrs. AIBN (0.4 g.; 0.0024 mole) was added and the charge was heated to 79±1° and agitated at that temperature for 24 hrs, after which the yellow liquid product was bottled. On cooling, the liquid solidified to a yellow crystalline solid. The material recovery was 209.4 g. (91.7%) plus 7.2 g. of samples removed for observation during the course of the reaction. The yellow solid showed a melting range of 71°–83°. Analysis by proton nuclear magnetic resonance (nmr) showed no evidence of olefinic double bond and a CH₂CH₂ to CH₂O+CHI ratio of 2.00:2.97 versus a ratio of 2.00 to 3.00 for

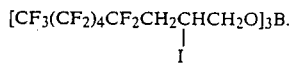
[CF₃(CF₂)₄CF₂CH₂CHCH₂O]₃B.
       |
       I

Hydrolysis

To 202 g. of the tris(2-iodo-3-perfluorohexylpropyl)-borate was added 200 ml. of deionized water. The mixture was heated under agitation at 100° for 20 minutes, yielding a two-layer system. The lower (product) layer was separated from the dark reddish-yellow aqueous phase at 90°–95°. Fresh deionized water (200 ml.) was added to the product and the mixture was heated under agitation at 100° for 0.5 hr. Separation of the layers at 90°–95° was followed by crystallization of the product layer. The ivory-white crystalline solid weighed 183.9 g. (91.5% of theory) (melting range 44°–47° with softening at 40°). Gas chromatographic assay was made, using a Perkin-Elmer Model 3920 flame ionization gas chromatograph, a 12'×⅛" stainless steel column packed with 20% GE SE-30 silicone on 80/100 chromosorb W-HP and a program of heating from 50° to 260° at 16°/minute. The analysis showed (area percent):

| | |
|---:|---:|
| Unknown | 4.8% |
| C₆F₁₃CH₂CHCH₂OH<br>      \|<br>      I | 95.2% |

EXAMPLE 2

Adduct Formation

Into a nitrogen-purged 250 ml. reaction flask were charged perfluorohexyl iodide (99.6% pure by gas chromatographic analysis) (200 g.; 0.447 mole) and triallyl borate (27.2 g.; 0.149 mole). With the charge blanketed by a slow, over-surface flow of nitrogen, the mixture was heated to 67°. AIBN (0.4 g.; 0.0024 mole) was added; agitation was continued at 67±2°, the resultant modest exotherm being controlled by air cooling of the reaction flask. Agitation at 67±2° was continued for 20 hrs., after which AIBN (0.4 g.; 0.0024 mole) was added. After agitation for 7 hrs. at 70±1°, AIBN (0.4 g.) was added; the charge was adjusted to 80±1°; and agitation was continued for 17.5 hrs. The charge, when bottled, solidified to an orange-yellow solid. The material recovery was 210.8 g. (92.3%) plus 8.6 g. of samples taken during the reaction.

A 2.7 g. sample of the reaction product taken just before bottling was mixed with 3 ml. of 1,1,2-trichloro-1,2,2-trifluoroethane and a few drops of water. The mixture was shaken vigorously at 20°–25° to hydrolyze the tris(2-iodo-3-perfluorohexylpropyl)borate. Layer separation was made and the solvent layer was analyzed by gas chromatography. The area percentages of the compounds formed (excluding the solvent) were:

| | |
|---:|---:|
| C₆F₁₃I | 1.81% |
| Unknown #1 | 0.61% |
| Unknown #2 | 3.14% |
| Unknown #3 | 0.43% |
| C₆F₁₃CH₂CHCH₂OH<br>      \|<br>      I | 94.0% |

No evidence was found for regeneration of allyl alcohol.

Hydrolysis

Tris-(2-iodo-3-perfluorohexylpropyl)borate (210.8 g.) was transferred to a reaction flask containing 211 ml. of water. The mixture was heated to 100°, forming a 2-layer system. The upper (aqueous) layer was yellow-brown, indicating free iodine; the color was discharged completely by the addition of sodium bisulfite (0.08 g.) as its 10% solution in water. The layers were separated at 95±5°; the bottom (product) layer was returned to the flask with 200 ml. of fresh deionized water, and was distilled through a 5-plate Oldershaw column to a final head temperature of 100° (pot temperature of 101°). The still pot contents were placed in a separatory funnel and the bottom, yellow layer was cut to a pan in which it solidified rapidly. The product, weighing 193.4 g. (92.2% of theory), melted in a range between 44° and 47°, with softening at 40°. Gas chromatographic analysis of the product showed 98.3% purity as 2-iodo-3-perfluorohexylpropanol.

EXAMPLE 3

Into a nitrogen purged flask were charged 99.6% pure perfluorohexyl iodide (125 g.; 0.279 mole), triallyl borate (17 g.; 0.093 mole) and dried 1,1,2,2-tetrachloroethylene. With the charge blanketed by nitrogen, the mixture was heated to 67° and AIBN (0.25 g.; 0.0015 mole) was added. Agitation at 67±1° for 0.3 hour showed a very slight exotherm. The temperature of the charge was adjusted to 70±1° and the charge agitated for 20 hours. AIBN (0.25 g.) was added and agitation at 70±1° continued for 7 hours. AIBN (0.25 g.) was again added; the charge was adjusted to 79±1°, and the mixture was agitated at 79±1° for 16.5 hrs., after which it was sampled for analysis. Cooling the charge to ~35° resulted in partial crystallization. The crystalline slurry was bottled at 25°; the material recovery was 245.3 g. (91.6%) plus 10.5 g. removed as samples during the reaction.

The 2.9 g. sample removed at the termination of the reaction was hydrolyzed by shaking with 3 ml. of a 75:25 mixture of water and acetone (3 ml.) and the organic material was extracted into 1,1,2-trichloro-1,2,2-trifluoroethane (3 ml). Gas chromatographic analysis (excluding the peaks for acetone, the chlorofluorocarbon solvent and the tetrachloroethylene) showed the composition (area %):

|  |  |
|---|---|
| $C_6F_{13}I$ | 1.3% |
| Unknowns | 2.5% |
| $C_6F_{13}CH_2CH(I)CH_2OH$ | 96.2% |

EXAMPLE 4

Adduct Formation

Two identical preparations were made, using perfluorohexyl iodide (400 g.; 0.897 mole), triallyl borate (54.4 g.; 0.299 mole) and AIBN (2.4 g.; 0.0146 mole). The reaction program involved addition of 0.8 g. AIBN to the iodide-borate mixture at 69±2°, followed by 19.5 hrs. agitation at 69±2°. The second 0.8 g. increment of AIBN was followed by 6.5 hrs. at 69±2°, and the third 0.8 g. increment by 19 hrs. agitation at 79±1°. Sampling and hydrolysis were carried out as in Example 3. Gas chromatographic analysis thereafter showed a 98% conversion of $C_6F_{13}I$ to borate adduct. In an effort to increase the conversion, the solid adducts from the two runs (840.5 g.) were mixed and diluted with 406 g. of tetrachloroethylene; triallyl borate (28.2 g.; 0.15 mole) and AIBN (1.0 g.; 0.006 mole) were added. The charge was heated under agitation at 78±1° for 24 hrs. A check on conversion showed no improvement over that obtained earlier. The perchloroethylene adduct mixture weighed 1260.8 g. (98.8% recovery).

Hydrolysis

A 100-gram portion of the tetrachloroethylene adduct mixture was hydrolyzed with 100 ml. of deionized water, and the mixture was steam distilled to a head temperature of 99° (pot temperature of 101°). The organic components in the still pot residue crystallized abruptly as the mixture was cooled under agitation to 46°-47°. After cooling to 25°, the crystalline residue was filtered and dried in vacuo at 20°-25° for 3 days to give 58.6 g. of a dry, colorless solid. Analyses were run as follows:

(a) Gas chromatography showed essentially pure

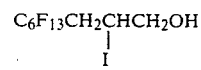

(b) Proton nmr spectra, examined as

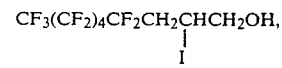

showed:

|  | Found | Calculated |
|---|---|---|
| $HO/OCH_2$ | 1.01:1.94 | 1:2 |
| $HO/CHI$ | 1.01:1.01 | 1:1 |
| $HO/CH_2CF_2$ | 1.01:2.03 | 1:2 |

(c) Infrared analysis showed a strong OH band and a spectrum consistent with the above-cited structure.

EXAMPLE 5

A mixture of perfluoroalkyl iodides was analyzed by gas chromatography and shown to have the following composition (area %):

$C_4F_9I$—1.0%
$C_6F_{13}I$—41.5%
$C_8F_{17}I$—29.8%
$C_{10}F_{21}I$—14.4%
$C_{12}F_{25}I$—7.6%
$C_{14}F_{29}I$—2.5%
Unknowns—3.2%

Based on that composition, the average molecular weight of the mixture calculated as $R_fI$ was 537.7.

The perfluoroalkyl iodide mixture (241.1 g.; 0.448 mole) and triallyl borate (27.2 g.; 0.149 mole) were heated in a nitrogen blanketed flask to 67°. AIBN (0.4 g.; 0.0024 mole) was added; a modest exotherm was experienced over the following 2.5 hrs, the charge being under agitation at 69±3°, and air cooling being enough to hold the temperature in the indicated limits. The charge was agitated for a total of 19.5 hrs at 70±2° after the first AIBN addition. A second AIBN increment (0.4 g.) was added and the charge was agitated at 70±2° for 7 hrs. AIBN (0.4 g.) was added; the charge was adjusted to 79±1°, and agitation was continued for 17 hrs. The charge was sampled for analysis and the yellow liquid bottled to give a crystalline yellow solid. The material recovery was 250.7 g. (93%) plus 9.1 g. of samples taken for analysis during the run.

The sample taken just before bottling was hydrolyzed as in Example 3 and the organic layer was analyzed by gas chromatography. Conversion of the individual $R_fI$ homologs was calculated by dividing the areas under the iodohydrin peaks by the sum of the iodohydrin and $R_fI$ homolog peak areas. Based on those calculations, the conversions were as follows:

$C_6F_{13}I$ to $C_6F_{13}CH_2CH(I)CH_2OH$—93.4%
$C_8F_{17}I$ to $C_8F_{17}CH_2CH(I)CH_2OH$—92.9%
$C_{10}F_{21}I$ to $C_{10}F_{21}CH_2CH(I)CH_2OH$—93.1%
$C_{12}F_{25}I$ to $C_{12}F_{25}CH_2CH(I)CH_2OH$—91.8%

EXAMPLE 6

Preparation of Triallyl Borate

A mixture of 6.5 lbs. (0.105 lb. mole) of boric acid, 30.7 lbs. (0.53 lb. mole) of allyl alcohol and 12.85 lbs. of toluene was refluxed at a pot temperature of 90°–105° at atmospheric pressure, using a column packed with ¼" porcelain saddles to effect separation, and a water separator to remove the by-product water from the entraining solvent. Reflux was continued until no more water collected in the separator (27 hrs.). The product mixture was distilled at atmospheric pressure to a pot temperature of 125° C., cooled to 25±5° and then stripped at 100±10 mm. absolute mercury pressure to a pot temperature of 65°; these operations removed in major part the excess allyl alcohol and the toluene solvent. The residue was 22.1 lbs. of colorless liquid product containing 87.4% of triallyl borate.

Adduct Formation

Analysis of a mixture of straight chain perfluoroalkyl iodides showed the following area % composition by gas chromatographic analysis:

Unknowns—2.0%
$C_4F_9I$—3.4%
$C_6F_{13}I$—44.6%
$C_8F_{17}I$—29.4%
$C_{10}F_{21}I$—13.4%
$C_{12}F_{25}I$—4.8%
$C_{14}F_{29}I$—1.6%
$C_{16}F_{33}I$—0.5%
$C_{18}F_{37}I$—0.2%
$C_{20}F_{41}I$—0.1%

The average molecular weight as $R_fI$ was 517.

To 827.2 g. of the above-described mixture (1.6 moles) was added crude triallyl borate (166.6 g. of 87.4% solution in toluene; 0.8 mole). The mixture was heated to 67±3° under agitation in a reactor topped with an anhydrous calcium sulfate-containing drying tube (used to prevent back diffusion of moist air). To the mixture was added AIBN (3.3 g.; 0.02 mole) and the charge was agitated at 67±3° for 3.5 hrs. AIBN (3.3 g.) was added and agitation was continued for 4 hrs. at 67±3°. A third increment of AIBN (3.3 g.) was added; the charge was set at 69±4° and agitation was continued for 17 hrs. The mixture was sampled (1 g.) and the sample hydrolyzed as in Example 3. Gas chromatographic analysis showed that approximately 99% of the perfluoroalkyl iodides had been converted to borate adducts or to reaction products with the free radicals generated by thermal decomposition of the AIBN initiator.

Hydrolysis

The entire charge of adduct was drowned into 5% sodium chloride brine (550 g.) and agitated to hydrolyze the borate adducts to a semi-gelatinous mass of products which thinned and separated to a two-layer system on heating to 90°–100°. The mixture was distilled at atmospheric pressure, using a 5-plate Oldershaw column. Distillation of the toluene, regenerated allyl alcohol and unreacted perfluoroalkyl iodides was terminated at a head temperature of 97.5° (pot temperature of 102°) because of solids crystallizing in the condenser [evidence of codistillation of $C_6F_{13}CH_2CH(I)CH_2OH$]. The residual material in the still pot (a two layer system) was separated at 90°–95°; the lower (product) layer crystallized on cooling to a pale yellow solid. The crude yield was 907.5 g. (98.6% of theory). Analysis of the product by gas chromatography showed the following area percentage composition:

Toluene—1.0%
Unknowns—3.0%
$C_{10}F_{21}I$—0.1%
$C_4F_9CH_2CH(I)CH_2OH$—3.6%
$C_6F_{13}CH_2CH(I)CH_2OH$—43.3%
$C_8F_{17}CH_2CH(I)CH_2OH$—28.0%
$C_{10}F_{21}CH_2CH(I)CH_2OH$—14.1%
$C_{12}F_{25}CH_2CH(I)CH_2OH$—4.9%
$C_{14}F_{29}CH_2CH(I)CH_2OH$—1.6%
$C_{16}F_{33}CH_2CH(I)CH_2OH$—0.4%

EXAMPLE 7

Adduct Formation

Analysis of a mixture of straight chain perfluoroalkyl iodides showed the following area percentage composition by gas chromatography:

Unknown—1.9%
$C_4F_9I$—1.6%
$C_6F_{13}I$—48.2%
$C_8F_{17}I$—41.0%
$C_{10}F_{21}I$—6.7%
$C_{12}F_{25}I$—0.6%

The average molecular weight as $R_fI$ was 502.6.

To 1660 g. of this perfluoroalkyl iodide composition (3.3 moles) was added triallyl borate (201.3 g.; 1.106 mole) and dry methyl ethyl ketone (382 g.). The charge was adjusted to a temperature of 68±3° under agitation, and the addition reaction was effected in accordance with the following schedule:

| Elapsed Time (hrs.) | Additions Made | | | |
|---|---|---|---|---|
| | Azobisisobutyronitrile | | Triallyl Borate | |
| | Grams | Moles | Grams | Moles |
| 0 | 2.0 | 0.012 | | |
| 20 | 2.0 | 0.012 | | |
| 44 | 2.0 | 0.012 | | |
| 51 | 2.0 | 0.012 | 49 | 0.27 |
| 77 | 2.0 | 0.012 | | |
| 79 | | | 49 | 0.27 |
| 99 | 0.7 | 0.004 | | |
| 129 | 3.0 | 0.018 | | |
| 145 | 3.0 | 0.018 | | |
| 172 | 2.0 | 0.018 | | |
| 196 | Terminated as complete | | | |

Sampling and hydrolysis (as in Example 3) after termination showed an average conversion of $R_fI$ to $R_fCH_2CH(I)CH_2OH$ components in excess of 97%.

Hydrolysis

The entire charge was drowned into 1300 ml. of 5% sodium chloride brine under agitation, and the hydrolyzed mass was steam stripped through a 5-plate Oldershaw column to a head temperature of 93.5°. Layer separation of the residue in the still pot yielded 1914.8 g of product (lower layer) which showed the following area percentage analysis by gas chromatography:

Methyl ethyl ketone—7.9%
Unknowns—0.7%
$C_4F_9CH_2CH(I)CH_2OH$—1.8%
$C_6F_{13}CH_2CH(I)CH_2OH$—48.2%
$C_8F_{17}CH_2CH(I)CH_2OH$—35.5%
$C_{10}F_{21}CH_2CH(I)CH_2OH$—5.9%

Preparation of triallyl borate

A mixture of 445.3 g. (7.2 moles) of boric acid, 2088 g. (36 moles) of allyl alcohol and 697 g. of toluene was refluxed at a pot temperature of 90°–105° and atmospheric pressure, using a column packed with 0.25 inch glass beads to effect separation, and a Dean-Stark separator to remove the by-product water from the solvent. Reflux was continued until no more water was collected in the Dean-Stark separator (27 hours). The product mixture was topped to a pot temperature of 145° to remove toluene and excess alcohol. The residue was distilled in vacuo through a 5-plate Oldershaw to yield 1287.4 g (98.2% of theory) of a colorless liquid product distilling at 62°–63° and 6.0 mm absolute mercury pressure.

Preparation of 3-perfluoroalkyliodohydrins

A mixture of perfluoroalkyl iodides was used which had the characteristics given below. The mixture was analyzed by gas chromatography, using a Perkin-Elmer Model 3920 flame ionization gas chromatograph, a 12'×18" stainless steel column packed with 20% GE SE-30 silicone on 80/100 Chromosorb W-HP and a program of heating from 50° C. to 260° C. at 16° C./minute. The homolog distribution was expressed as area % and the average molecular weight calculated therefrom to give the following:

Unknowns—1.9%
$C_4F_9I$—1.6%
$C_6F_{13}I$—48.2%
$C_8F_{17}I$—41.0%
$C_{10}F_{21}I$—6.7%
$C_{12}F_{25}I$—0.6%
$C_{14}F_{29}I$—<0.1%

Average molecular weight as $R_fI = 502.8$.

A mixture of 1296 g. (2.58 moles) of the above-described $R_fI$, 156.4 g (0.86 moles) of triallyl borate and 300 g. of methyl ethyl ketone was heated to 65±2°. "Vazo" 64 azobisisobutyronitrile was added (2.1 g.; 0.013 mole); there was a barely discernible but definite exotherm lasting approximately 15 minutes. The reaction temperature was adjusted to 69±4°, and the charge was agitated at this temperature for about 18 hours, followed by addition of increments of "Vazo" 64 and triallyl borate at intervals as follows: 2.1 g. of "Vazo" 64; 7 hours later—39.1 g. (0.215 mole) of triallyl borate and 2.1 g. of "Vazo" 64; 17 additional hours—39.1 g. of triallyl borate and 2.1 g. of "Vazo" 64; 28 hours thereafter—2.1 g. "Vazo" 64; and 8 hours later—1.05 g. of "Vazo" 64. After a total of 96 hours, the charge was sampled and the sample hydrolyzed with aqueous acetone and the hydrolyzed sample extracted into "F-113" 1,1,2-trichloro-1,2,2-trifluoroethane. Gas chromatographic analysis of the "F-113" layer showed essentially 98.6% conversion of $R_fI$ to 3-perfluoroalkylpropylene iodohydrins. The charge was added to 1300 g. of water; the mixture was steam stripped through a 5-plate Oldershaw column to a head temperature of 92° (pot temp. 96°+) to remove unreacted allyl alcohol and the major portion of the MEK. The two phase still residue was separated at ~90°, the lower (product) layer being bottled and the upper (aqueous) layer being discarded, to yield 1431 g. (91%) of a pale yellow oil which solidified on cooling.

Analysis (area % and mol. wt. calculated therefrom): $C_4F_9CH_2CHICH_2OH$—1.4%; $C_6F_{13}CH_2CHICH_2OH$—48.9%; $C_8F_{17}CH_2CHICH_2OH$—34.4%; $C_{10}F_{21}CH_2CHICH_2OH$—5.5%; MEK and other non-iodohydrins—9.7%.

Average molecular weight as

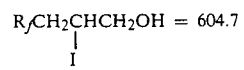

I claim:

1. A borate or mixture of borates represented by the formula:

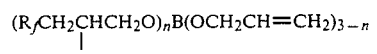

wherein
$R_f$ is $C_4$–$C_{20}$ perfluoroalkyl; and
n is an average number between about 1.5 and about 3.

2. The borate or mixture of claim 1 wherein n is an average number between about 1.7 and about 2.5.

3. The borate or mixture of borates of claim 2 wherein n is an average number between about 1.7 and about 2.0.

4. Mixtures of compounds of claim 1, 2 or 3 wherein 80–90% of the $R_f$ groups contain about 6 to about 12 carbons.

5. Mixtures of claim 1, 2 or 3, wherein 80–90% of said $R_f$ groups contain about 6 to about 10 carbon atoms.

6. Mixtures of claim 1, 2 or 3 wherein the average of the chain lengths in the $R_f$ groups is about 6 to about 8 carbons.

7. A process for preparing a borate or mixture of borates of claim 1 comprising reacting $R_fI$ and triallyl borate, at an $R_fI$:triallyl borate mole ratio between about 1.5:1 and about 3:1, in the presence of a small but effective amount of a free radical initiator, wherein $R_f$ is as defined in claim 1.

8. The process of claim 7 further characterized in that a borate or mixture of borates of claim 1 is drowned in water at a temperature above the freezing point of any of said borates so as to hydrolyze said borate or mixture of borates to form an iodohydrin represented by the formula:

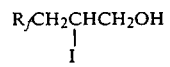

wherein $R_f$ is as defined in claim 1.

9. The process of claim 7 or 8 wherein said mole ratio is between about 1.7:1 and about 2.5:1.

10. The process of claim 7 or 8 wherein said mole ratio is between about 1.7:1 and about 2:1.

11. The process of claim 7 or 8 wherein 80–90% of the $R_f$ groups contain about 6 to about 12 carbons.

12. The process of claim 11 wherein said mole ratio is between about 1.7:1 and about 2.5:1.

13. The process of claim 11 wherein said mole ratio is between about 1.7:1 and about 2:1.

14. The process of claim 7 or 8 wherein 80–90% of said $R_f$ groups contain about 6 to about 10 carbons.

15. The process of claim 14 wherein said mole ratio is between about 1.7:1 and about 2.5:1.

16. The process of claim 14 wherein said mole ratio is between about 1.7:1 and about 2:1.

17. The process of claim 7 or 8 wherein the average of the chain lengths in $R_f$ is between about 6 and about 8 carbons.

18. The process of claim 17 wherein said mole ratio is between about 1.7:1 and about 2.5:1.

19. The process of claim 17 wherein said mole ratio is between about 1.7:1 and about 2:1.

* * * * *

UNITED STATES PATENT OFFICE
CERTIFICATE OF CORRECTION

PATENT NO. : 4,489,006
DATED : December 18, 1984
INVENTOR(S) : Stanley Earl Krahler It is certified that error appears in the above-identified patent and that said Letters Patent are hereby corrected as shown below:

The paragraph which commences at Column 1, line 7, should read:

This application is a continuation of application Ser. No. 470,174 filed Feb. 28, 1983, now abandoned, which is a continuation-in-part of application Serial No. 306,594, filed September 28, 1981, which in turn is a continuation of Serial No. 119,148, filed February 6, 1980. This application is also a continuation-in-part of application Serial No. 260,609, filed May 6, 1981, which is a divisional of U.S. application Serial No. 092,767, filed November 9, 1979, now U.S. Patent 4,283,533.

Column 10, lines 10 and 11 should read:

$$(R_f CH_2 \underset{I}{C}HCH_2 O)_n B(OCH_2 CH=CH_2)_{3-n}$$

Signed and Sealed this

Second Day of July 1985

[SEAL]

Attest:

DONALD J. QUIGG

Attesting Officer    Acting Commissioner of Patents and Trademarks